United States Patent
Spielberg et al.

(10) Patent No.: US 10,596,105 B2
(45) Date of Patent: Mar. 24, 2020

(54) ORGANIC NASAL TREATMENT SOLUTION

(71) Applicants: Max Spielberg, Beverly Hills, CA (US); David Johnson, Beverly Hills, CA (US)

(72) Inventors: Max Spielberg, Beverly Hills, CA (US); David Johnson, Beverly Hills, CA (US)

(*) Notice: Subject to any disclaimer, the term of this patent is extended or adjusted under 35 U.S.C. 154(b) by 0 days.

(21) Appl. No.: 15/912,766

(22) Filed: Mar. 6, 2018

(65) Prior Publication Data

US 2019/0000752 A1 Jan. 3, 2019

Related U.S. Application Data

(60) Provisional application No. 62/526,446, filed on Jun. 29, 2017.

(51) Int. Cl.
| | |
|---|---|
| *A61K 9/00* | (2006.01) |
| *A61K 47/12* | (2006.01) |
| *A61K 47/10* | (2017.01) |
| *A61K 36/752* | (2006.01) |
| *A61K 47/02* | (2006.01) |

(52) U.S. Cl.
CPC .......... *A61K 9/0043* (2013.01); *A61K 36/752* (2013.01); *A61K 47/02* (2013.01); *A61K 47/10* (2013.01); *A61K 47/12* (2013.01)

(58) Field of Classification Search
CPC ...... A61K 9/0043; A61K 47/12; A61K 47/10; A61K 47/02; A61K 36/752
See application file for complete search history.

(56) References Cited

U.S. PATENT DOCUMENTS

| | | | |
|---|---|---|---|
| 2014/0377389 A1* | 12/2014 | Budman | A61K 9/0043 424/769 |
| 2017/0079281 A1* | 3/2017 | Methot | A23L 3/3472 |
| 2017/0246262 A1* | 8/2017 | Latefi | A61K 9/0043 |

FOREIGN PATENT DOCUMENTS

DE 19917836 * 10/2000

OTHER PUBLICATIONS

Azwanida, A review on the extraction methods use in medicinal plants, principal, strength and limitation, Medicinal & Aromatic Plants, vol. 4, issue 3, 2015.*

* cited by examiner

*Primary Examiner* — Mina Haghighatian
(74) *Attorney, Agent, or Firm* — David W Barman

(57) ABSTRACT

A nasal spray or therapy solution is provided having organic glycerin; an organic preservative system containing glycerin, *citrus reticulata* fruit extract, *citrus aurantium amara* fruit extract, *citrus aurantium sinensis* peel extract, ascorbic acid, citric acid, lactic acid, water; sodium chloride; water; whereby said nasal spray exhibits inhibited bacteriological growth in vitro for up to 36 months.

6 Claims, No Drawings

ORGANIC NASAL TREATMENT SOLUTION

INDEX TO RELATED APPLICATIONS

This application is a non-provisional of, and claims benefit to U.S. Provisional Patent Application Ser. No. 62/526,446 filed Jul. 5, 2017 the disclosure of which is incorporated herein by reference in its entirety.

BACKGROUND OF THE INVENTION

Typically, nasal cavity solution therapy, including nasal sprays, mists, vaporizers and the like containing salt, which are commonly used to treat cold and allergies and to ease congestion, are either sterilized using gamma-radiation or contain preservative systems full of unhealthy, synthetic, often harmful, ingredients.

Until this invention, there were no certified organic, healthy nasal sprays available. One reason for this includes the fact that commonly known preservatives are synthetic and often harmful and unhhealthy.

The present invention has discovered novel formulations for addressing this current need.

SUMMARY OF THE INVENTION

The present invention is for therapy solutions delivered to the nasal cavity. These solutions include, but are not limited to: nasal sprays; nasal mist; solids mixed into solution at time of use into delivery systems such as vaporizers, neti pots and other such systems; nasal solution therapy packets; and the like.

In one embodiment, the present invention is a nasal spray or therapy solution comprising:
1-4% w/w organic glycerin;
0.1-4% w/w of an organic preservative system containing Glycerin, *citrus reticulata* fruit extract, *citrus aurantium amara* fruit extract, *citrus aurantium sinensis* peel extract, ascorbic acid, citric acid, lactic acid, water;
0.2-1.0% w/w sodium chloride; and
91-98.3% Water; whereby said nasal spray exhibits inhibited bacteriological growth in vitro for up to 36 months.

In one embodiment, the present invention is a nasal spray or therapy solution comprising:
1.5-2.5% w/w organic glycerin;
0.5-2% w/w of an organic preservative system containing Glycerin, *citrus reticulata* fruit extract, *citrus aurantium amara* fruit extract, *citrus aurantium sinensis* peel extract, ascorbic acid, citric acid, lactic acid, water;
0.4-0.7% w/w sodium chloride; and
94.5-98% water; whereby said nasal spray exhibits inhibited bacteriological growth in vitro for up to 36 months.

In one embodiment, the present invention is a nasal spray or therapy solution consisting of:
2.0% w/w organic glycerin;
0.5% w/w of an organic preservative system containing Glycerin, *citrus reticulata* fruit extract, *citrus aurantium amara* fruit extract, *citrus aurantium sinensis* peel extract, ascorbic acid, citric acid, lactic acid, water;
0.65% w/w sodium chloride; and
96.5% water; whereby said nasal spray exhibits inhibited bacteriological growth in vitro for up to 36 months.

In one embodiment, the organic preservative system is a solution comprising:
Glycerin, 50-70%
*citrus reticulata* fruit extract, 0.01-1.00%
*citrus aurantium amara* fruit extract, 0.01-1.00%
*citrus aurantium sinensis* peel extract, 0.01-1.00%
ascorbic acid, 0.01-1.00%
citric acid, 0.1-2.0%
lactic acid, 0.1-2.0%
water q.s.

In one embodiment, the organic preservative system is a solution consisting of:
Glycerin, 50-70%
*citrus reticulata* fruit extract, 0.01-1.00%
*citrus aurantium amara* fruit extract, 0.01-1.00%
*citrus aurantium sinensis* peel extract, 0.01-1.00%
ascorbic acid, 0.01-1.00%
citric acid, 0.1-2.0%
lactic acid, 0.1-2.0%
water q.s.

In one embodiment, the organic preservative system is free of grapefruit extracts.

DETAILED DESCRIPTION OF THE PREFERRED EMBODIMENT

Persons with knowledge of nasal spray formulations are familiar with the various excipients and preservatives available to the formulator. These include those materials that are listed in the US Food and Drug Administration guide—Generally regarded as safe (GRAS).

However, one who is trying to make a healthy, certified organic product cannot use synthetic, harmful preservatives and cannot use irradiation because irradiation is not allowed in a certified organic product.

In formulations practice, it is known that often two or more preservatives are provided. Sometimes they are provided for specific preserving characteristics. However, there are preservative systems that are utilized with various components having beneficial synergistic affects even though the exact mechanism of the beneficial synergistic affects is not clearly understood. This is true in the present formulation whereby a synergistic system has been discovered, demonstrated effective, yet is operating in a mechanism not fully understood.

The nasal mucosal pH is approximately 5.5-6.5, and increases in rhinitis to 7.2-8.3.

Based on this, it is often desirable to provide nasal drops and sprays as dilute saline solutions.

Although in general saline sprays are safe for extended use, there are reports of contraindications and reaction to various preservatives commonly used in these sprays. This includes not only allergic reactions to the preservatives, but initial and increased sensitivities to the preservatives.

In response to this, some sprays are available as "sterilized" and provided to the consumer after irradiation.

After a significant number of failed efforts, the inventors have discovered the following preservative system, when incorporated into the nasal spray of the present invention, has produced desirable results.
Glycerin, 50-70%
*citrus reticulata* fruit extract, 5.00-15.00%
*citrus aurantium amara* fruit extract, 5.00-15.00%
*citrus aurantium sinensis* peel extract, 5.00-15.00%
ascorbic acid, 2.00-5.00%
citric acid, 0.1-2.0%
lactic acid, 0.1-2.0%
water q.s.

In one embodiment, the system is formulated as follows:
Glycerin, 55-65%
*citrus reticulata* fruit extract, 10.00-14.00%
*citrus aurantium amara* fruit extract, 10.00-14.00%

*citrus aurantium sinensis* peel extract, 10.00-14.00%
ascorbic acid, 2.00-5.00%
citric acid, 0.1-2.0%
lactic acid, 0.1-2.0%
water q.s.

Although the exact synergy is not fully known or understood, results appear favorable when the following ratio of components is used:
*citrus reticulata* fruit extract: *citrus aurantium amara* fruit extract:*citrus aurantium sinensis* peel extract:glycerine: ascorbic acid:citric acid:lactic acid:water
1:0.9-1.1:0.9-1.1:4.5-5.0:0.05-0.2:0.05-0.2:0.05-0.2.

As a starting point the inventors began with the following formula:

| Formula 1 | |
|---|---|
| Sodium Chloride (NaCl) | 0.65% w/v |
| Water | 99.35% |

This formula does not provide a desired result as there was no preservative system, and it could not be sterilized with gamma irradiation since such sterilization is not allowed in an organic product.

The inventors investigated numerous formulations incorporating organic components believed to impart preservative properties.

The various systems led to the utilization of a preservative system including multiple components.

Ultimately, after extensive research and development, the components were narrowed down to the systems stated below.

After various trials, the following formula is tested:

| | |
|---|---|
| 2.0% Organic Glycerin 0.5% certified organic preservative system: Glycerin, *citrus reticulata* fruit extract, *citrus aurantium amara* fruit extract, *citrus aurantium sinensis* peel extract, ascorbic acid, citric acid, lactic acid, water. 0.65% Sodium Chloride (NaCl) Remaining 96.85% is water | Formula 2 |

| | |
|---|---|
| 2.0% Organic Glycerin 0.2% certified organic preservative system: Glycerin, *citrus reticulata* fruit extract, *citrus aurantium amara* fruit extract, *citrus aurantium sinensis* peel extract, ascorbic acid, citric acid, lactic acid, water. 0.65% Sodium Chloride (NaCl) Remaining 97.15% is water | Formula 3 |

Regarding formulas 2 and 3, this is the first time anyone has successfully used an organic preservative system in a nasal saline spray.

Table 1 shows test results over 28 days for bacteriological growth using drops prepared according to Formula 2. Test done according to USP 40-2017 Antimicrobial Effectiveness Testing <51>

| | | 2D ( ) | 7D ( ) | 14D ( ) | 21D ( ) | 28D ( ) |
|---|---|---|---|---|---|---|
| Saline Spray/Drops JR041817-01 Acc# 14251 | | | | | | |
| Staph | Inocula- | <10 | <10 | <10 | | |
| E. coli | tion | <10 | <10 | <10 | | |
| Ps. aer | Date: | <10 | <10 | <10 | | |
| Candida | | | <10 | <10 | <10 | |
| Asp | | 80cfu | <10 | <10 | | |

| | | 2D ( ) | 7D ( ) | 14D ( ) | 21D ( ) | 28D ( ) |
|---|---|---|---|---|---|---|
| Saline Spray/Drops JR041817-02 Acc# 14252 | | | | | | |
| Staph | Inocu- | <10 | <10 | <10 | | |
| E. coli | lation | <10 | <10 | <10 | | |
| Ps. aer | Date: | <10 | <10 | <10 | | |
| Candida | | | <10 | <10 | <10 | |
| Asp | | $1.3 \times 10^2$ | <10 | <10 | | |

Thus, as seen in the above table, the present invention, without utilizing preservatives of irradiation, inhibits bacteriological growth for at least 28 days.

Additional preliminary data at time points up to and including 12, 18, 24, 30 and 36 months indicate continued inhibition of bacteriological growth.

Table 2 shows test results over 28 days for bacteriological growth using drops prepared according to Formula 3. Testing done according to USP 40-2017 Antimicrobial Effectiveness Testing <51>

RESULTS: TABLE SUMMARY

| | Preservative Testing Colony Forming Units/gram | | | | | |
|---|---|---|---|---|---|---|
| Organism | Inoculam/g | Day 2 | Day 7 | Day 14 | Day 21 | Day 28 |
| *Staphylococcus aureus* (bacteria) (ATCC# 6538) | $1.25 \times 10^6$ | <10 | <10 | <10 | <10 | <10 |
| *Escherichia coli* (bacteria) (ATCC# 8739) | $1.5 \times 10^6$ | <10 | <10 | <10 | <10 | <10 |
| *Pseudomonas aeruginosa* (bacteria) (ATCC# 9027) | $1.2 \times 10^6$ | <10 | <10 | <10 | <10 | <10 |
| *Candida albicans* (yeast) (ATCC# 10231) | $1.4 \times 10^5$ | <10 | <10 | <10 | <10 | <10 |
| *Asperigillus niger* (mold) (ATCC# 16404) | $1.3 \times 10^5$ | $1.30 \times 10^2$ | <10 | <10 | <10 | <10 |

LOG REDUCTION CALCULATION FROM INITIAL INOCULUM

| | 14 DAYS | 28 DAYS |
|---|---|---|
| *Asperigillus niger* | 4.00 | 4.00 |
| *Candida albicans* | 4.00 | 4.00 |
| *Escherichia coli* | 5.00 | 5.00 |
| *Pseudomonas aeruginosa* | 5.00 | 5.00 |
| *Staphylococcus aureus* | 5.00 | 5.00 |

Validation of results from Table 2.

RESULTS:

| | Preservative Testing Validation | | | | |
|---|---|---|---|---|---|
| Organism | Inoculum | Dilution | Microbial Recovery | Diluent | Percent Recovery |
| *Staphylococcus aureus* | 25 cfu/plate | 1:10 | 24 cfu/plate | LB | 96% |
| *Escherichia coli* | 31 cfu/plate | 1:10 | 28 cfu/plate | LB | 90% |
| *Pseudomonas aeruginosa* | 47 cfu/plate | 1:10 | 42 cfu/plate | LB | 89% |

-continued

RESULTS:

Preservative Testing Validation

| Organism | Inoculum | Dilution | Microbial Recovery | Diluent | Percent Recovery |
|---|---|---|---|---|---|
| *Candida albicans* | 97 cfu/plate | 1:10 | 91 cfuplate | LB | 93% |
| *Asperigillus niger* | 28 cfu/plate | 1:10 | 24 cfu/plate | LB | 85% |

CFU = colony forming units
Diluent: Letheen broth
LB = Letheen Broth
Dilution: 1:10

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

What is claimed:

1. A nasal spray or therapy solution comprising:
   1-4% w/w organic glycerin;
   0.5-4% w/w of an organic preservative system containing additional glycerin, *citrus reticulata* fruit extract, *citrus aurantium amara* fruit extract, *citrus aurantium sinensis* peel extract, additional ascorbic acid, additional citric acid, lactic acid, and water;
   0.2-1.0% w/w sodium chloride; and
   91-98.3% additional water; all percentages based on total weight, whereby said nasal spray exhibits reduced bacteriological growth in vitro for up to 36 months.

2. The nasal spray or therapy solution of claim 1 comprising:
   1.5-2.5% w/w organic glycerin;
   0.5-2% w/w of an organic preservative system containing additional glycerin, *citrus reticulata* fruit extract, *citrus aurantium amara* fruit extract, *citrus aurantium sinensis* peel extract, additional ascorbic acid, additional citric acid, lactic acid, and water;
   0.4-0.7% w/w sodium chloride; and
   91-98.3% additional water; all percentages based on total weight, whereby said nasal spray exhibits reduced bacteriological growth in vitro for up to 36 months.

3. A nasal spray or therapy solution consisting of:
   2.0% w/w organic glycerin;
   0.5% w/w of an organic preservative system consisting additional glycerin, *citrus reticulata* fruit extract, *citrus aurantium amara* fruit extract, *citrus aurantium sinensis* peel extract, additional ascorbic acid, additional citric acid, lactic acid, and water;
   0.65% w/w sodium chloride; and
   96.5% additional water; all percentages based on total weight, whereby said nasal spray exhibits reduced bacteriological growth in vitro for up to 36 months.

4. The nasal spray or therapy solution of claim 1, wherein said organic preservative system comprises a component ratio: *citrus reticulata* fruit extract:*citrus aurantium amara* fruit extract:*citrus aurantium sinensis* peel extract:glycerine:ascorbic acid:citric acid:lactic acid:water of:
   1:0.9-1.1:0.9-1.1:4.5-5.0:0.05-0.2:0.05-0.2:0.05-0.2.

5. The nasal spray or therapy solution of claim 2, wherein said organic preservative system comprises a component ratio: *citrus reticulata* fruit extract: *citrus aurantium amara* fruit extract:*citrus aurantium sinensis* peel extract:glycerine:ascorbic acid:citric acid:lactic acid:water of:
   1:0.9-1.1:0.9-1.1:4.5-5.0:0.05-0.2:0.05-0.2:0.05-0.2.

6. A nasal spray or therapy solution consisting of:
   2.0% w/w organic glycerin;
   0.5% w/w of an organic preservative system consisting of a component ratio: *citrus reticulata* fruit extract: *citrus aurantium amara* fruit extract:*citrus aurantium sinensis* peel extract:glycerine:ascorbic acid:citric acid:lactic acid:water of:
   1:0.9-1.1:0.9-1.1:4.5-5.0:0.05-0.2:0.05-0.2:0.05-0.2,
   0.65% w/w sodium chloride; and
   96.5% water; all percentages based on total weight, whereby said nasal spray exhibits reduced bacteriological growth in vitro for up to 36 months.

* * * * *